(12) United States Patent
Kim et al.

(10) Patent No.: US 11,524,210 B2
(45) Date of Patent: Dec. 13, 2022

(54) METHOD AND PROGRAM FOR PROVIDING REMOTE REHABILITATION TRAINING

(71) Applicant: NEOFECT CO., LTD., Seongnam-si (KR)

(72) Inventors: Hyang Jung Kim, Yongin-si (KR); Hyung Jun Park, Seoul (KR); Jin Young Kim, Seongnam-si (KR); Hyun Jung Roh, Seongnam-si (KR)

(73) Assignee: NEOFECT CO., LTD., Seongnam-si (KR)

( * ) Notice: Subject to any disclaimer, the term of this patent is extended or adjusted under 35 U.S.C. 154(b) by 165 days.

(21) Appl. No.: 16/728,973

(22) Filed: Dec. 27, 2019

(65) Prior Publication Data

US 2021/0031074 A1 Feb. 4, 2021

Related U.S. Application Data

(63) Continuation of application No. PCT/KR2019/018616, filed on Dec. 27, 2019.

(30) Foreign Application Priority Data

Jul. 29, 2019 (KR) ........................ 10-2019-0092039
Dec. 27, 2019 (KR) ........................ 10-2019-0176085

(51) Int. Cl.
*A63B 24/00* (2006.01)
*A63B 23/16* (2006.01)
*A63B 71/06* (2006.01)
*A63B 22/00* (2006.01)

(52) U.S. Cl.
CPC .......... *A63B 24/0075* (2013.01); *A63B 23/16* (2013.01); *A63B 71/0622* (2013.01); *A63B 2022/0094* (2013.01); *A63B 2071/0647* (2013.01); *A63B 2220/806* (2013.01); *A63B 2225/20* (2013.01)

(58) Field of Classification Search
CPC . A63B 24/0075; A63B 23/16; A63B 71/0622; A63B 2022/0094; A63B 2071/0647; A63B 2220/806; A63B 2225/20
See application file for complete search history.

(56) References Cited

U.S. PATENT DOCUMENTS

| | | | | |
|---|---|---|---|---|
| 8,620,146 B1 * | 12/2013 | Coleman | ................ | H04N 5/765 386/230 |
| 9,011,316 B2 * | 4/2015 | Mertens | ................ | G16H 20/30 600/38 |
| 9,154,739 B1 * | 10/2015 | Nicolaou | ................ | H04N 7/18 |

(Continued)

*Primary Examiner* — Malina D. Blaise
(74) *Attorney, Agent, or Firm* — Studebaker & Brackett PC

(57) ABSTRACT

A method for providing remote rehabilitation training is provided. The method includes receiving, by a server, a connection request from a user terminal and a therapist terminal, receiving, by the server, first image data, about an appearance where a user performs rehabilitation training using a rehabilitation training device, in real time from the user terminal, receiving, by the server, second image data, provided to the user who is performing the rehabilitation training, in real time from a rehabilitation training display device, and transmitting, by the server, the received first image data and the received second image data to the therapist terminal in real time.

12 Claims, 11 Drawing Sheets

(56) References Cited

U.S. PATENT DOCUMENTS

| | | | |
|---|---|---|---|
| 9,350,951 B1* | 5/2016 | Rowe | G06T 7/66 |
| 9,472,119 B2* | 10/2016 | Selvaraj | G09B 19/00 |
| 9,656,119 B2* | 5/2017 | Ura | A63B 24/0003 |
| 10,555,688 B1* | 2/2020 | Berme | A61B 5/4848 |
| 10,835,781 B2* | 11/2020 | Sands | A63B 24/0062 |
| 10,902,741 B2* | 1/2021 | Rubinstein | A63B 24/0062 |
| 10,922,997 B2* | 2/2021 | Rubinstein | A61B 5/0022 |
| 11,030,918 B2* | 6/2021 | Wallach | G09B 19/0038 |
| 2011/0039659 A1* | 2/2011 | Kim | A63B 24/0006 |
| | | | 482/8 |
| 2011/0257566 A1* | 10/2011 | Burdea | A63B 24/0006 |
| | | | 601/24 |
| 2012/0000300 A1* | 1/2012 | Sunagawa | A61B 5/4023 |
| | | | 73/865.4 |
| 2012/0154510 A1* | 6/2012 | Huitema | H04N 7/142 |
| | | | 348/E7.083 |
| 2012/0183939 A1* | 7/2012 | Aragones | G16H 20/30 |
| | | | 434/247 |
| 2012/0253484 A1* | 10/2012 | Burich | G16H 40/67 |
| | | | 700/91 |
| 2013/0115583 A1* | 5/2013 | Gordon | G16H 20/60 |
| | | | 434/247 |
| 2013/0115584 A1* | 5/2013 | Gordon | A63B 69/00 |
| | | | 434/247 |
| 2013/0123667 A1* | 5/2013 | Komatireddy | A61B 5/746 |
| | | | 600/595 |
| 2014/0172460 A1* | 6/2014 | Kohli | G16H 30/20 |
| | | | 705/3 |
| 2014/0200432 A1* | 7/2014 | Banerji | G16H 20/30 |
| | | | 607/54 |
| 2014/0214443 A1* | 7/2014 | Duffy | G16H 20/60 |
| | | | 705/2 |
| 2015/0004581 A1* | 1/2015 | Selman | G09B 19/0038 |
| | | | 434/257 |
| 2015/0072327 A1* | 3/2015 | Beaulieu | G16H 50/20 |
| | | | 434/257 |
| 2015/0355711 A1* | 12/2015 | Rihn | G06F 3/04815 |
| | | | 340/407.2 |
| 2016/0271438 A1* | 9/2016 | Weisz | A63B 21/159 |
| 2016/0331304 A1* | 11/2016 | Libey | A63F 13/212 |
| 2017/0032207 A1* | 2/2017 | Yoon | H04N 21/4316 |
| 2017/0069218 A1* | 3/2017 | Shin | G05D 1/0016 |
| 2017/0076619 A1* | 3/2017 | Wallach | G09B 19/0038 |
| 2017/0157512 A1* | 6/2017 | Long | A63F 13/497 |
| 2017/0161432 A1* | 6/2017 | Horseman | G06F 3/04815 |
| 2018/0120947 A1* | 5/2018 | Wells | G16H 40/67 |
| 2018/0261120 A1* | 9/2018 | Shiomi | G09B 9/00 |
| 2018/0271738 A1* | 9/2018 | Sapin | A61H 1/0237 |
| 2018/0304118 A1* | 10/2018 | French | G16H 50/30 |
| 2019/0088152 A1* | 3/2019 | Adamovich | A61B 5/1128 |
| 2019/0111299 A1* | 4/2019 | Radcliffe | A61H 1/0244 |
| 2019/0130788 A1* | 5/2019 | Seaton | G02B 27/017 |
| 2020/0094122 A1* | 3/2020 | Yamazaki | G06Q 50/20 |

* cited by examiner

METHOD AND PROGRAM FOR PROVIDING REMOTE REHABILITATION TRAINING

CROSS-REFERENCE TO RELATED APPLICATIONS

The present application is a continuation of International Patent Application No. PCT/KR2019/018616, filed on Dec. 27, 2019 which is based upon and claims the benefit of priority to Korean Patent Application Nos. 10-2019-0092039 filed on Jul. 29, 2019 and 10-2019-0176085 filed on Dec. 27, 2019. The disclosures of the above-listed applications are hereby incorporated by reference herein in their entirety.

BACKGROUND

Embodiments of the inventive concept described herein relate to a method and program for providing rehabilitation training.

Recently, with the development of online technology, remote rehabilitation training for checking a state of a patient in a situation where a therapist and the patient are far apart from each other and performing and coaching rehabilitation training have been frequently performed.

However, according to existing remote rehabilitation training, when a patient views a screen of a rehabilitation training display device independent of a user terminal on which the patient makes a video call with a therapist and performs rehabilitation training, it is possible for the therapist to view only the appearance of the patient who performs rehabilitation training and it is impossible for the therapist to view a training screen provided to the user (patient). Thus, it is difficult to perform accurate coaching.

SUMMARY

Embodiments of the inventive concept provide a method for providing rehabilitation training to provide an appearance where a patient performs rehabilitation training and a training screen, provided to a patient, to a therapist at the same time.

Embodiments of the inventive concept provide a method for providing rehabilitation training to simply discover a rehabilitation training display device, which provides a training screen to a user who is performing rehabilitation training, based on user account information.

Embodiments of the inventive concept provide a method for providing rehabilitation training to allow a therapist to record a memo for a state or rehabilitation training of a patient or write a related document in real time.

Embodiments of the inventive concept provide a method for providing rehabilitation training to allow a therapist to evaluate a state or rehabilitation training of a patient and change training settings such as a training curriculum and a daily life mission.

According to an exemplary embodiment, a method for providing remote rehabilitation training may include receiving, by a server, a connection request from a user terminal and a therapist terminal, receiving, by the server, first image data, about an appearance where a user performs rehabilitation training using a rehabilitation training device, in real time from the user terminal, receiving, by the server, second image data, provided to the user who is performing the rehabilitation training, in real time from a rehabilitation training display device, and transmitting, by the server, the received first image data and the received second image data to the therapist terminal in real time. The rehabilitation training display device may be connected with the rehabilitation training device in a wireless or wired manner and may provide the second image data which is a screen about rehabilitation training using the rehabilitation training device to the user.

Furthermore, in another embodiment, the first image data may be provided to a first layer in a therapist terminal screen and the second image data may be provided to a second layer in the therapist terminal screen, depending on a request of a therapist for the provision of the first image data and the second image data a therapist for the provision of the first image data and the second image data transmitted to the therapist terminal by the server.

Furthermore, in another embodiment, the therapist terminal screen may further include a third layer depending on a request of the therapist. The third layer may provide text data or image data input from the therapist or may provide text data or image data transmitted and received between the therapist and the user.

Furthermore, in another embodiment, the receiving of the connection request may include receiving, by the server, user account information input to the user terminal and therapist account information input to the therapist terminal and receiving, by the server, a remote rehabilitation training connection request from the user terminal and the therapist terminal. The receiving of the second image data may include discovering, by the server, a rehabilitation training display device corresponding to the user account information based on the user account information input to the user terminal and receiving, by the server, the second image data in real time from the discovered rehabilitation training display device.

Furthermore, in another embodiment, the discovering of the rehabilitation training display device may include discovering a rehabilitation training display device to which the same account information as the user account information input to the user terminal is input.

Furthermore, in another embodiment, the method may further include matching, by the server, identification values of one or more rehabilitation training display devices to specific user account information. The identification value may be differently assigned for each specific rehabilitation training display device. The discovering of the rehabilitation training display device may include discovering a rehabilitation training display device of an identification value matched to the user account information input to the user terminal.

Furthermore, in another embodiment, the method may further include receiving, by the server, user training change information from the therapist terminal. The user training change information may be information about training settings including a training type, training strength, a training rate, or a training period for the rehabilitation training performed by the user.

Furthermore, in another embodiment, the method may further include changing, by the server, training settings of the user, stored in user account information, based on the training change information received from the therapist terminal.

According to an exemplary embodiment, a server device for providing remote rehabilitation training may include a communication unit that receives a connection request from a user terminal and a therapist terminal, receives first image data, about an appearance where a user performs rehabilitation training using a rehabilitation training device, in real time from the user terminal, receives second image data, provided to the user who is performing the rehabilitation training, in real time from a rehabilitation training display device, and transmits the received first image data and the received second image data to the therapist terminal in real time and a controller that controls the communication unit. The rehabilitation training display device may be connected with the rehabilitation training device in a wireless or wired manner and may provide the second image data which is a screen about rehabilitation training using the rehabilitation training device to the user. The first image data may be provided to a first layer in a therapist terminal screen and the second image data may be provided to a second layer in the therapist terminal screen, depending on a request of a therapist for the provision of the first image data and the second image data a therapist for the provision of the first image data and the second image data transmitted to the therapist terminal by the communication unit.

According to an exemplary embodiment, a program for providing remote rehabilitation training may be combined with hardware and may be stored in a medium to execute the method for providing the remote rehabilitation training.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
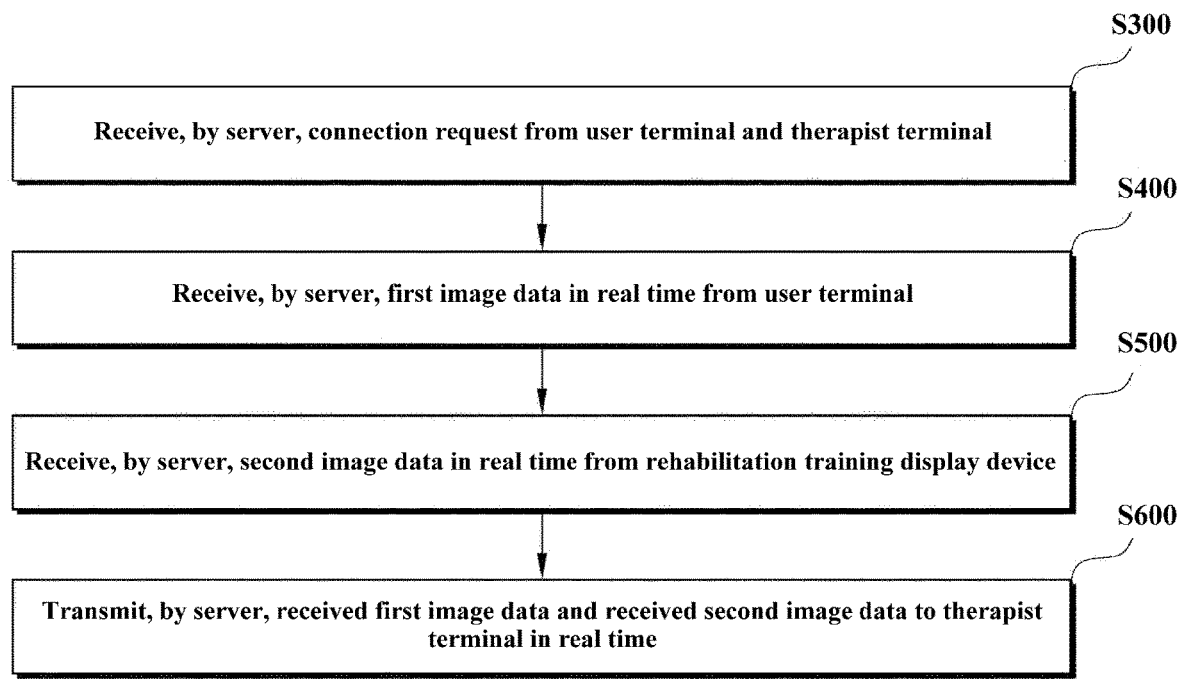
FIG. 1 is a block diagram illustrating a system for providing remote rehabilitation training according to an embodiment of the inventive concept.

Advantages, features, and methods of accomplishing the same will become apparent with reference to embodiments described in detail below together with the accompanying drawings. However, the inventive concept is not limited by embodiments disclosed hereinafter, and may be implemented in various forms. Rather, these embodiments are provided to so that this disclosure will be through and complete and will fully convey the concept of the invention to those skilled in the art, and the inventive concept will only be defined by the appended claims.

Terms used in the specification are used to describe embodiments of the inventive concept and are not intended to limit the scope of the inventive concept. In the specification, the terms of a singular form may include plural forms unless otherwise specified. The expressions "comprise" and/or "comprising" used herein indicate existence of one or more other elements other than stated elements but do not exclude presence of additional elements. Like reference numerals designate like elements throughout the specification, and the term "and/or" may include each of stated elements and one or more combinations of the stated elements. The terms such as "first" and "second" are used to describe various elements, but it is obvious that such elements are not restricted to the above terms. The above terms are used only to distinguish one element from the other. Thus, it is obvious that a first element described hereinafter may be a second element within the technical scope of the inventive concept.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

The term 'computer' in the specification may include all of various devices capable of performing arithmetic processing. For example, the computer may correspond to a smartphone, a tablet personal computer (PC), a cellular phone, a personal communication service (PCS) phone, a synchronous/asynchronous international mobile telecommunication-2000 (IMT-2000) mobile terminal, a palm PC, a personal digital assistant (PDA), or the like as well as a desktop PC or a notebook.

The term 'user 100' in the specification refers to a user who performs rehabilitation training using a rehabilitation training device, that is, a patient.

The term 'therapist 150' refers to a person who checks and analyzes a state of the user and coaches the user for rehabilitation training.

The terms 'user terminal 500' and 'therapist terminal 400' in the specification refer to all devices, each of which includes a communication function, in which the user and the therapist are able to install and use a program (or application). In other words, the terminal may include various communication devices such as a cellular phone, a PCS phone, a synchronous/asynchronous IMT-2000 mobile terminal, a palm PC, a PDA, a smartphone, a wireless application protocol (WAP) phone, a mobile game console, a table PC, a smart watch, a notebook PC, a desktop PC, a smart camera, and a smart TV. Furthermore, the terminal may include a device which does not basically include a communication function, but is capable of performing communication by being combined with a memory chip having the communication function.

The term 'rehabilitation training device 700' in the specification refers to all devices used to perform rehabilitation training by the user and is not limited to a specific rehabilitation training device.

The term 'rehabilitation training display device 600' refers to a display device which provides a training screen for assisting the user to perform rehabilitation training to the user when the user performs specific rehabilitation training using the rehabilitation training device.

The term 'first image data 810' in the specification refers to image data about an appearance where the user performs rehabilitation training using the rehabilitation training device, obtained from the user terminal.

The term 'second image data 820' in the specification refers to a training screen for assisting the user to perform rehabilitation training, which is provided to the user via the rehabilitation training display device. For example, the term 'second image data 820' may refer to a game screen provided to the user by the rehabilitation training display device when the user performs rehabilitation training which is gamed to interwork with the rehabilitation training device.

The term 'third image data 830' in the specification may refer to image data about an appearance of the therapist, obtained from the therapist terminal.

Hereinafter, an embodiment of the inventive concept will be described in detail with reference to the accompanying drawings.

FIG. 1 is a block diagram illustrating a system for providing remote rehabilitation training according to an embodiment of the inventive concept.

Referring to FIG. 1, the system for providing the remote rehabilitation training according to an embodiment of the inventive concept may include a rehabilitation training device 700 used for rehabilitation training by a user 100, a rehabilitation training display device 600, a user terminal 500 in which a program or application for remote rehabilitation training is installed, a therapist terminal 400 in which the program is installed for remote rehabilitation training of the therapist 150 with the user 100, and a server 300 for receiving first image data in real time from the user terminal 500, receiving second image data in real time from the rehabilitation training display device 600, and transmitting the received data to the therapist terminal 400.

The user 100 may perform rehabilitation training using the rehabilitation training device 700 which assists in rehabilitation training and the rehabilitation training display device 600 which provides a training screen. The user terminal 500 in which the program for providing remote rehabilitation training is installed may obtain an appearance where the user 100 performs rehabilitation training and may transmit the obtained information to the server 300 in real time.

Figure 2:
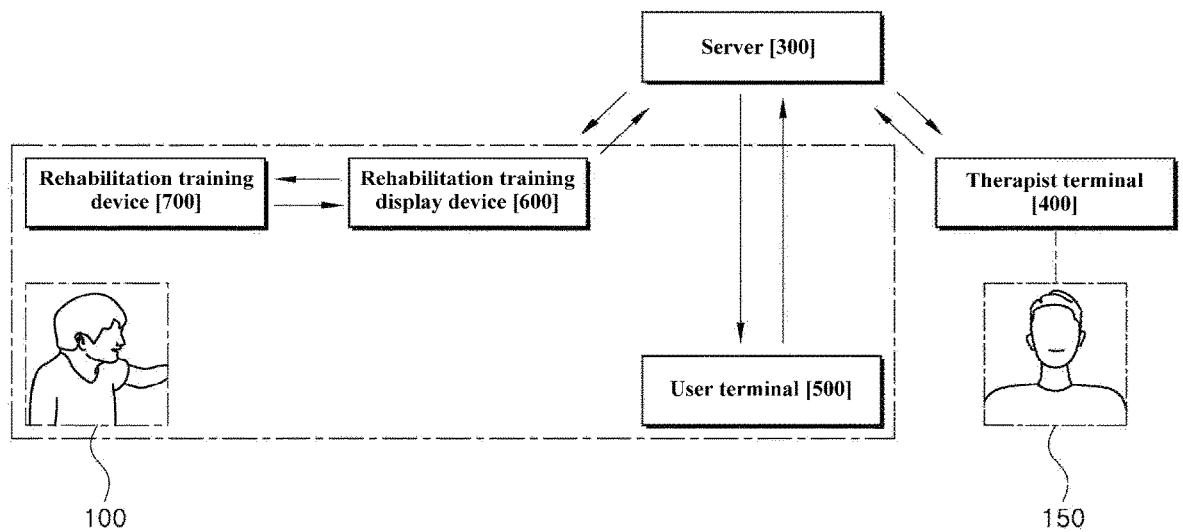
FIG. 2 is a drawing illustrating an appearance where a user performs rehabilitation training, according to an embodiment of the inventive concept.

For example, as shown in FIG. 2, the user 100 may perform a gamed finger motion rehabilitation training using a finger rehabilitation glove 700. A tablet PC 600 of the user 100 may provide second image data 820, which is a game screen of the gamed finger motion rehabilitation training, to the user 100. In other words, in this case, the user 100 may perform the gamed rehabilitation training using the finger rehabilitation glove 700 to suit the game screen 820 while viewing the game screen 820 of the tablet PC 600. Furthermore, the user terminal 500, in which the application for providing remote rehabilitation training is installed, may capture the first image data 810, which is a training appearance of the user 100, and may transmit the captured data to the server 300 in real time.

The therapist 150 may access the program for providing remote rehabilitation training, installed in the therapist terminal 400, for remote rehabilitation training with the user 100. For example, the therapist 150 may access the program for providing remote rehabilitation training, installed in the PC 400, or a webpage and may receive first image data 810 or second image data 820 from the server 300.

The server 300 may receive the first image data 810 in real time from the user terminal 400, may receive the second image data 820 in real time from the rehabilitation training display device 600, and may transmit the received data to the therapist terminal 400 in real time.

In an embodiment, prior to performing remote rehabilitation training between the user 100 and the therapist 200, the server 300 may provide a questionnaire for checking a state of the user (patient) 100 through the program for providing remote rehabilitation training, installed in the user terminal 500, and may match the patient 100 with the therapist 150 based on the state of the patient 100.

Furthermore, in an embodiment, prior to providing the questionnaire for checking the state of the user 100, the server 300 may collect a variety of information including basic information of the patient 100, such as a name of the patient 100, age of the patient 100, gender of the patient 100, and a time when a disorder occurs, information necessary to check a state of the patient 100, and the like.

Providing the questionnaire for checking the state of the patient 100 may be to provide one or more questionnaires capable of dividing a disorder state into several groups to the patient 100.

The server 300 may provide one or more questionnaires. As the user 100 selects YES or NO for each questionnaire using the user terminal 500, the server 300 may determine whether the patient 100 belongs to any group. Moreover, when matching a therapist to each patient and providing rehabilitation training to each patient, the therapist terminal 400 may receive information of a group to which the patient 100 belongs from the server 300.

When it is determined that the patient 100 belongs to any group, the server 300 may transmit a predetermined patient state message indicating, for example, whether the patient 100 is in any state or whether it is effective to perform any training, to the patient 100 to suit the group corresponding to the patient 100.

Thereafter, the server 300 may propose one or more suitable missions depending on a state of the patient 100, that is, each group. The server 300 may provide contents of a mission selected by the user terminal 500 among the one or more missions to the patient 100.

The suitable mission may be a mission suitable for a state of the patient 100 among the one or more missions, which may be preset for each group and may be determined by an algorithm for recommending suitable training to the patient 100 by collecting data.

When the suitable mission is proposed by the algorithm which recommends the suitable training to the patient 100, the proposed mission may be varied as data is accumulated. In other words, as data is accumulated, a more suitable mission may be provided to each patient.

Furthermore, after the server 300 and the therapist terminal 400 according to an embodiment of the inventive concept are connected to each other, when the therapist 150 directly determines a mission suitable for a corresponding group using the therapist terminal 400 and transmits the determined mission to the server 300, the server 300 may provide the mission to the patient 100.

The mission may be roughly classified as a daily life mission, an interworking training game mission, or an information reading mission.

The daily life mission may include all of actions persons do routinely. The daily life mission may include all of actions persons do in everyday life, for example, 'Share your daily life on the SNS', 'Drink a glass of water', and 'Turn on TV'. Whether the daily life mission is performed may be determined through an input indicating that the performance of the mission is completed after the mission is performed.

The interworking training game mission may be a training game mission of a corresponding interworking service, with which a service unit for providing specific rehabilitation training interworks. Herein, the service unit may refer to an application, a web site, or a program.

The information reading mission may be a mission provided such that a corresponding patient reads information necessary for a state of the patient. Herein, the information provided to be read by the patient may be information provided in an environment for providing a service according to an embodiment of the inventive concept. Alternatively, the information provided to be read by the patient may be information provided by an external service rather than the service according to an embodiment of the inventive concept. A link or interworking service may be provided such that the patient accesses the information.

In an embodiment, a method for providing remote rehabilitation training may further include interworking with a separate service which provides a mission before providing a questionnaire for checking a state of the patient 100.

To interwork with the separate service (hereinafter referred to as "interworking service"), the server 300 may collect information such as an ID or an e-mail of the interworking service from the user 100 and may provide the collected information to perform authentication with the interworking service.

Furthermore, in an embodiment, the method for providing the remote rehabilitation training may further include receiving the result of performing a mission of the patient 100. Receiving the result of performing the mission may be to check a state where the patient 100 performs a mission, manage a training plan of the patient 100, or collect data.

When receiving the result of performing the mission to collect the data, the server 300 may design an algorithm for recommending suitable training to the patient 100 through statistics or learning based on information about criteria capable of being classified as the data is collected, a type of training performed, or the result of performing training.

The designed algorithm may recommend and provide more accurate training depending on a group of divided patients.

Hereinafter, a description will be given in detail of a method for providing remote rehabilitation training between a user and a therapist.

Figure 3:
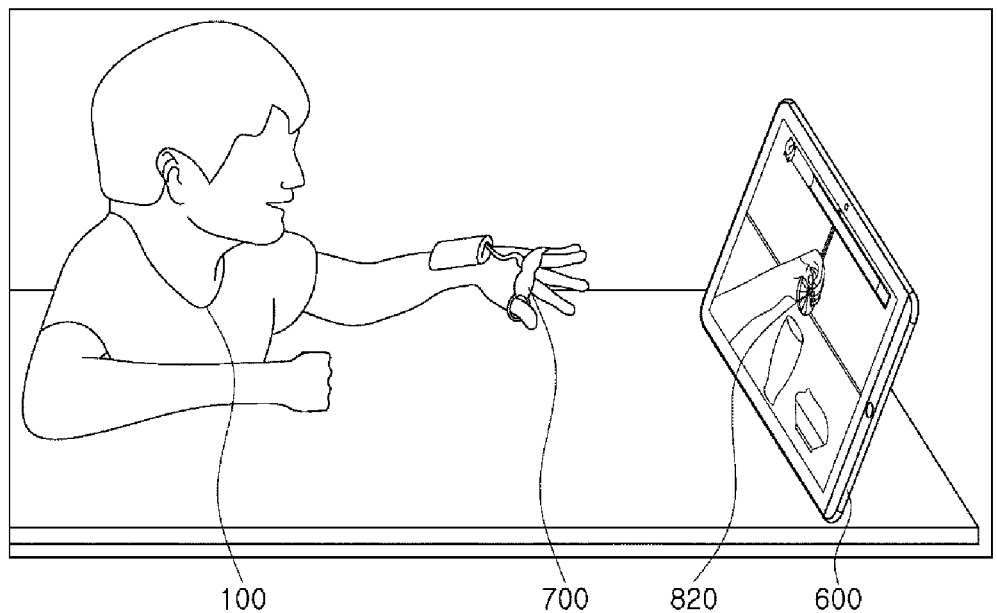
FIG. 3 is a flowchart illustrating a method for providing remote rehabilitation training according to an embodiment of the inventive concept.

Referring to FIG. 3, the method for providing the remote rehabilitation training according to an embodiment of the inventive concept may include receiving (S300), by a server, a connection request from a user terminal and a therapist terminal, receiving (S400), by the server, first image data about an appearance where a user performs rehabilitation training using a rehabilitation training device in real time from the user terminal, receiving (S500), by the server, second image data, provided to the user who is performing the rehabilitation training, in real time from a rehabilitation training display device, and transmitting (S600), by the server, the received first image data and the received second image data to the therapist terminal in real time. Hereinafter, a description will be given in detail of each operation.

In S300, a server 300 of FIG. 1 may receive the connection request from a user terminal 500 and a therapist terminal 400 of FIG. 1. The connection request refers to a connection request for remote rehabilitation training between a user 100 and a therapist 150 of FIG. 1 and is not limited to the manner.

For example, when the user 100 and the therapist 150 do not face each other and perform and coach rehabilitation training through a video call, the connection request may refer to a video call connection request.

In an embodiment, the connection request may include transmitting, by one of the user 100 or the therapist 150, a remote rehabilitation training request and transmitting, by the other, an approval request for the remote rehabilitation training request.

In another embodiment, the connection request may include accessing, by each of the user 100 and the therapist 150, a program for providing remote rehabilitation training, installed in each of the user terminal 500 and the therapist terminal 400, on date and time which are preset between the user 100 and the therapist 150 who are connected to each other.

Figure 5:
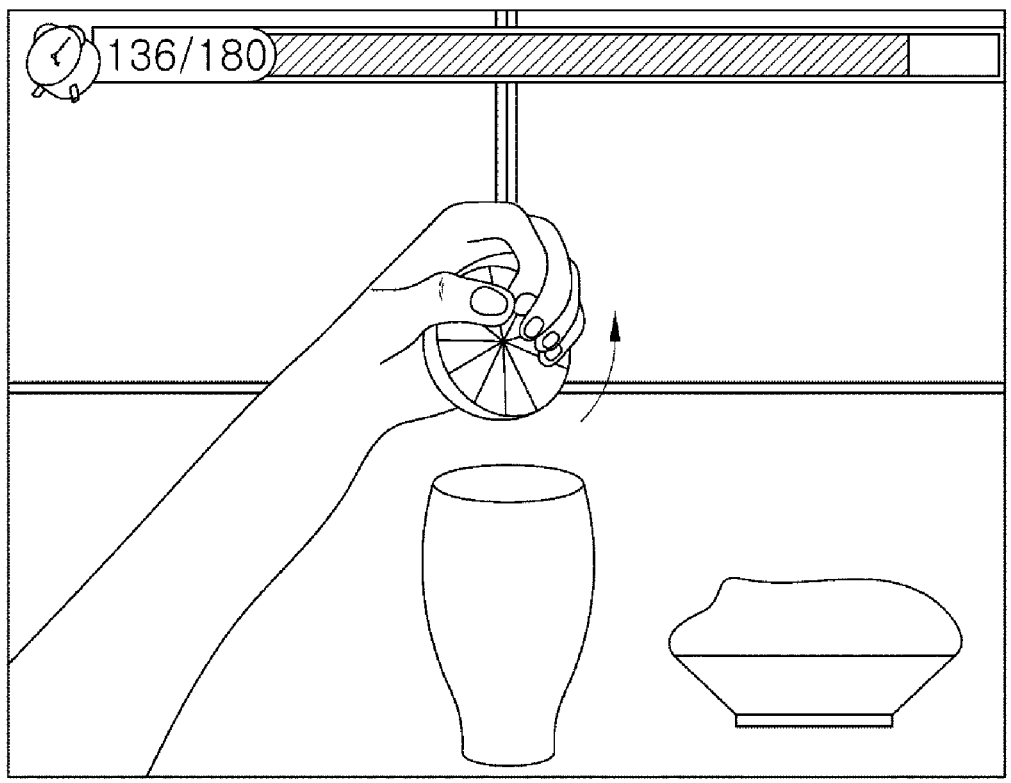
FIG. 5 is a drawing illustrating second image data according to an embodiment of the inventive concept.

Referring to FIG. 5, in an embodiment, the receiving (S300) of the connection request may include receiving (S310), by the server, user account information input to the user terminal and therapist account information input to the therapist terminal and receiving (S320), by the server, a remote rehabilitation training connection request from the user terminal and the therapist terminal.

In an embodiment, the user account information or the therapist account information may refer to account information of a user or therapist who logs in to the program for providing remote rehabilitation training, installed in the user terminal 500 or the therapist terminal 400.

In S400, the server 300 may receive first image data, about an appearance where the user 100 performs rehabilitation training using the rehabilitation training device 700, in real time from the user terminal 500.

In an embodiment, in performing rehabilitation training, the user 100 may use the rehabilitation training device 700.

Furthermore, in another embodiment, in performing the rehabilitation training, the user 100 may use a rehabilitation training display device 600, which provides a training screen for the rehabilitation training, as well as the rehabilitation training device 700.

As described above, first image data 810 of FIG. 4 may be image data about an appearance where the user 100 performs rehabilitation training using the rehabilitation training device 700.

In an embodiment, the first image data 810 may include image data when the user 100 performs rehabilitation training by only the rehabilitation training device 700.

In another embodiment, the first image data 810 may include image data when the user 100 performs rehabilitation training using both the rehabilitation training device 700 and the rehabilitation training display device 600. In this case, the rehabilitation training display device 600 may be included in the first image data 810 as shown in FIG. 2, or the rehabilitation training display device 600 may fail to be included in the first image data 810 as shown in FIG. 4.

In other words, as described below, because the first image data 810 is to provide an appearance where the user 100 performs rehabilitation training using the rehabilitation training device 700 to the therapist 150, the user 100 and the rehabilitation training device 700 which is in use by the user 100 may be key elements.

Figure 4:
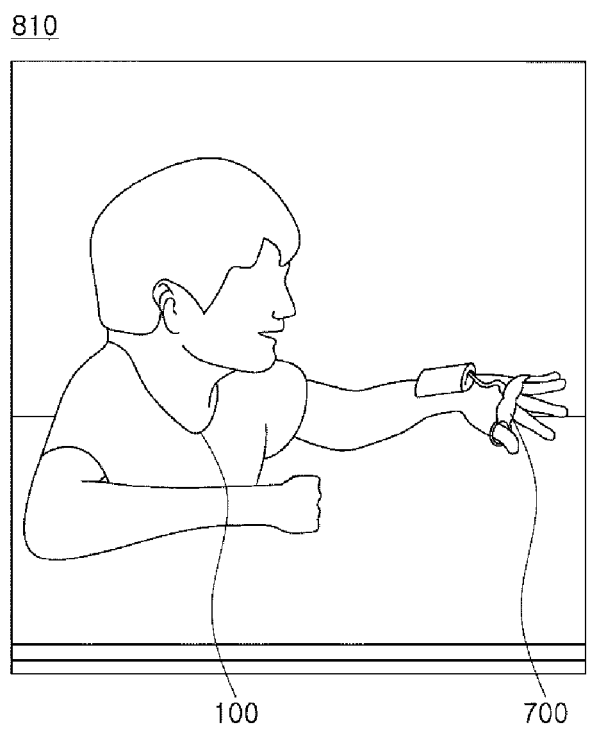
FIG. 4 is a drawing illustrating first image data according to an embodiment of the inventive concept.

For example, as shown in FIG. 2 or 4, the first image data 810 refers to image data in which the user terminal 500 captures an appearance where the user 100 performs finger motion rehabilitation training using a finger rehabilitation glove 700.

In S500, the server 300 may receive second image data 820, provided to the user 100 who is performing the rehabilitation training, in real time from the rehabilitation training display device 600.

In an embodiment, the rehabilitation training display device 600 may be connected with the rehabilitation training device 700 of the user 100 through a wireless or wired connection. The wireless connection may include on or more of wireless-fidelity (Wi-Fi), light-fidelity (Li-Fi), Bluetooth, ultra wide band (UWB), Zigbee, and Z-wave, but not limited thereto.

As described above, the second image data 820 may be a training screen for assisting the user 100 to perform rehabilitation training, which is provided to the user 100 via the rehabilitation training display device 600.

For example, as shown in FIG. 5, when the user 100 performs gamed rehabilitation training for squeezing juice from an orange through motion of the hand using the finger rehabilitation glove 700, the tablet PC 600 which is the rehabilitation training display device may provide the second image data 820, which is a game screen on which a hand-shaped graphic object, output to correspond to hand motion of the user 100, squeezes juice from an orange, to the user 100 and the user 100 may perform rehabilitation training while viewing a screen of the tablet PC 600.

However, the second image data 820 is not limited to the game screen of the rehabilitation training, and refers to all screens provided from the rehabilitation training display device 600 to the user 100.

Figure 6:
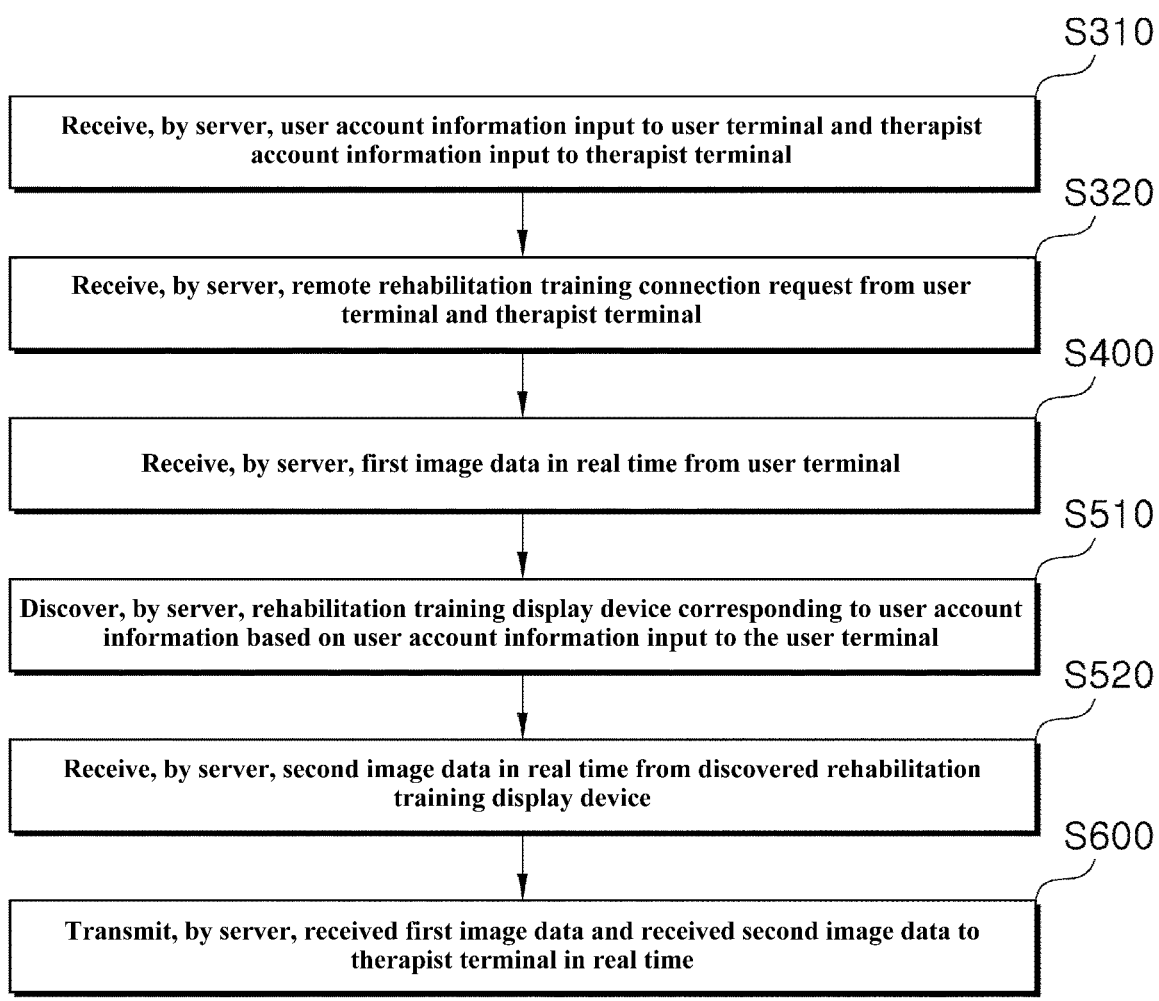
FIG. 6 is a flowchart illustrating a method for providing remote rehabilitation training, which further includes receiving account information and discovering a rehabilitation training display device, according to an embodiment of the inventive concept.

Referring again to FIG. 6, in an embodiment, the receiving S500 of the second image data may include discovering (S510), by the server, a rehabilitation training display device corresponding to user account information based on the user account information input to the user terminal and receiving (S520), by the server, the second image data in real time from the discovered rehabilitation training display device.

In S510, the server 300 may discover the rehabilitation training display device corresponding to the user account information based on the user account information input to the user terminal 500.

In other words, in an embodiment, to receive the second image data about rehabilitation training which is currently being performed by a specific user, the server 300 may discover a rehabilitation training display device which is in use by the user, based on account information of the user who logs in to a program for providing remote rehabilitation training, installed in the user terminal 500.

In an embodiment, the discovering may include discovering a rehabilitation training display device to which the same account information as the user account information input to the user terminal 500 is input.

For example, after a program or application for providing remote rehabilitation training is installed in the tablet PC which is the rehabilitation training display device 600 as well as the smartphone which is the user terminal 500 to be logged in, when the user 100 is performing rehabilitation training, the server 300 may discover a tablet PC to which the same account information as the user account information which is logged in to the application of the smartphone, which is received in S310, is logged in.

According to the above embodiment, although the user 100 uses various rehabilitation training display devices which are not registered in advance, the server 300 may simply discover a rehabilitation training display device which is in use by the user 100, using account information which is logged in to a program installed in the rehabilitation training display device.

Figure 7:
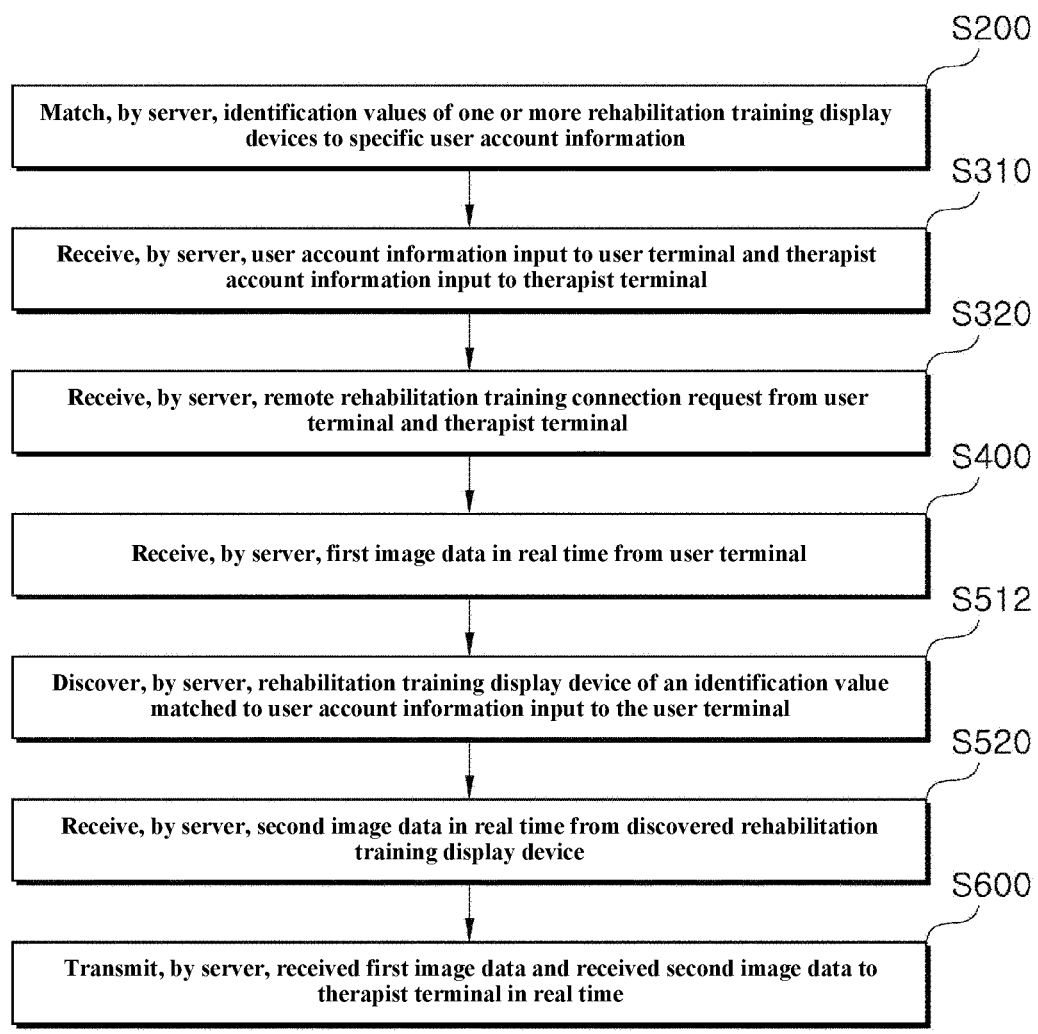
FIG. 7 is a flowchart illustrating a method for providing remote rehabilitation training to discover a rehabilitation training display device using an identification value matched to user account information according to an embodiment of the inventive concept.

Referring to FIG. 7, in another embodiment, the discovering may include discovering (S512) a rehabilitation training display device of an identification value matched to the user account information input to the user terminal.

In an embodiment, the identification value may be differently assigned for each specific rehabilitation training display device and may include, for example, a product number assigned for each specific rehabilitation training display device Furthermore, in an embodiment, the method for providing the remote rehabilitation training may further include matching (S200), by the server, identification values of one or more rehabilitation training display devices to specific user account information, prior to discovering (S512) the rehabilitation training display device based on the identification value.

In other words, by registering a rehabilitation training display device used by a specific user with account information of the specific user in advance (by matching an identification value to user account information), the server 300 may simply discover the registered rehabilitation training display device based on the account information when the user performs specific rehabilitation training.

According to the above embodiment, although the user account information is not input to the rehabilitation training display device (e.g., a separate program is not installed), the server 300 may simply discover the rehabilitation training display device used by the user 100 by matching the previously registered identification value.

In S520, the server 300 may receive the second image data in real time from the discovered rehabilitation training display device. In other words, the server 300 may receive the second image data 820, about a screen provided to the user 100, in real time from the rehabilitation training display device 600 discovered by the above-mentioned method.

In S600, the server 300 may transmit the received first image data and the received second image data to the therapist terminal 400 in real time. In other words, in an embodiment, the server 300 may transmit first image data about an appearance where a specific user (a specific patient) is performing rehabilitation training and second image data which is a screen provided to the user to a terminal of a specific therapist (e.g., a dedicated therapist of a specific patient) matched to the specific user (the specific patient) in real time, such that the therapist monitors rehabilitation training of the patient in real time.

In an embodiment, the first image data may be provided to a first layer 410 in a therapist terminal screen and the second image data may be provided to a second layer 420 in the therapist terminal screen depending on a request of the therapist 150 for the provision of the first image data and the second image data transmitted to the therapist terminal 400 by the server 300. In other words, the server 300 may divide the therapist terminal screen to display the first image data and the second image data on one screen.

In an embodiment, whether to provide the first layer 410 or the second layer 420, that is, whether to provide the first image data 810 or the second image data 820 may be freely determined according to a request of the therapist 150.

Figure 8:
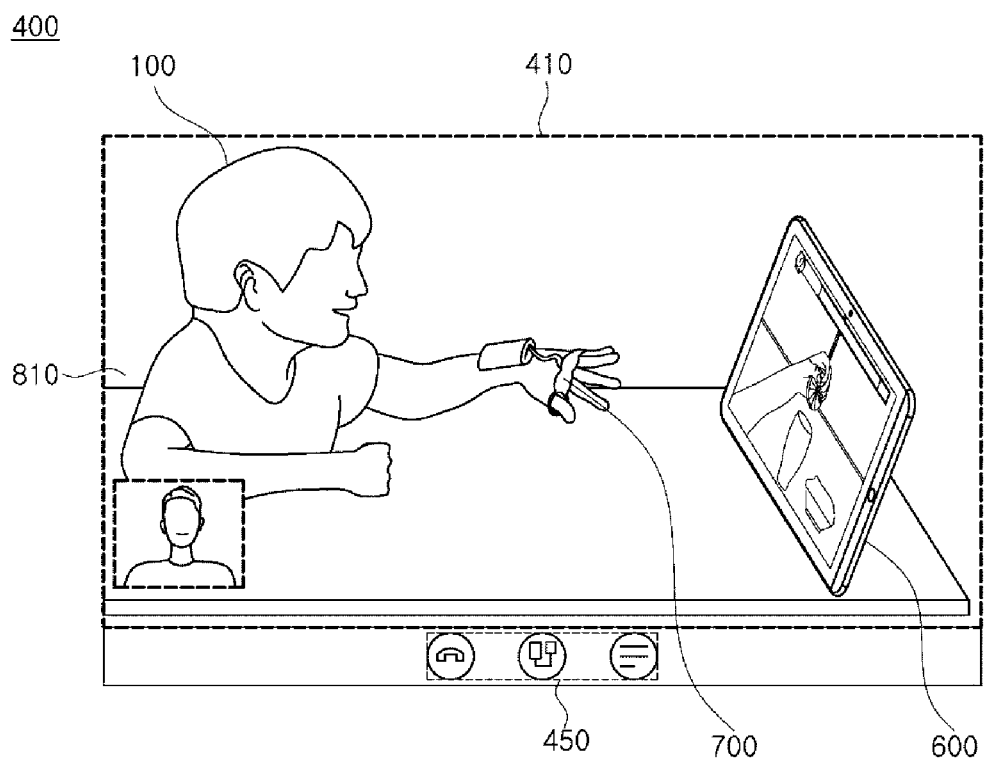
FIGS. 8 and 9 are drawings illustrating therapist terminal screens to which first image data or second image data is provided according to an embodiment of the inventive concept.
Figure 9:
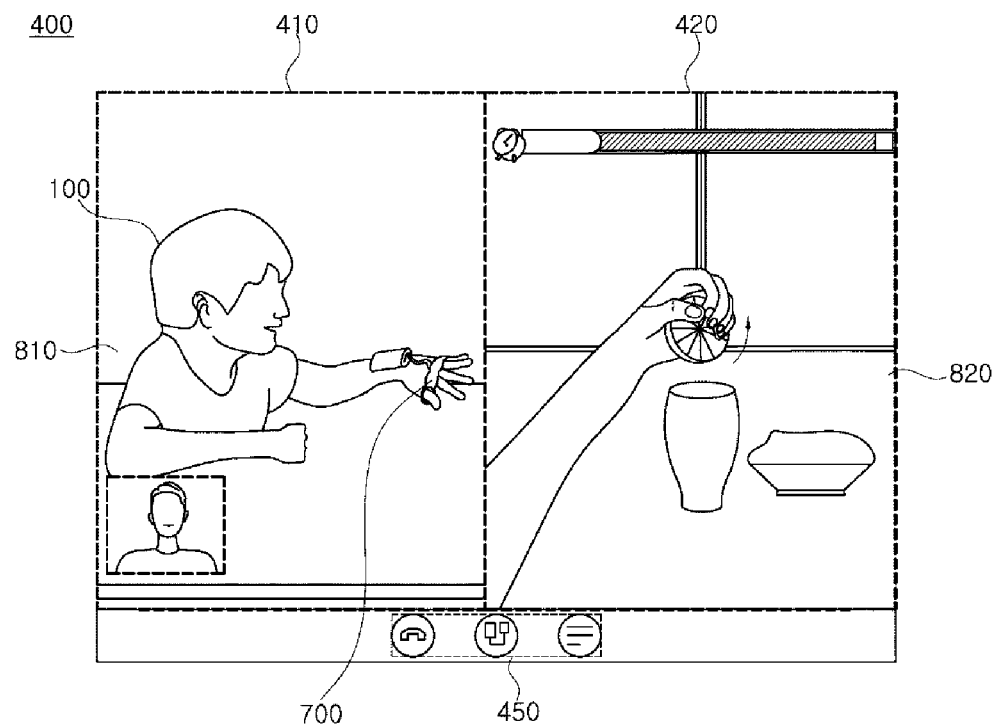

FIGS. 8 and 9 are drawings illustrating therapist terminal screens to which first image data or second image data is provided according to an embodiment of the inventive concept.

In an embodiment, as shown in FIG. 8, a screen of a therapist terminal (e.g., PC) may include only a first layer 410 which provides first image data 810 where a user 100 performs rehabilitation training.

In another embodiment, as shown in FIG. 9, a screen of a therapist PC may further include a second layer 420 which provides second image data 820 which is a game screen provided from a rehabilitation training display device to a user 100. In this case, a therapist may identify a game screen applied to the user 100 as well as the appearance of the user 100 who is performing rehabilitation training on one screen, such that it is possible to perform more effective rehabilitation training.

In an embodiment, like conversion from FIG. 8 to FIG. 9, whether to provide first image data or second image data may be freely determined according to a request of the therapist. For example, whether to provide the first image data or the second image data may be determined according to selection of the therapist for a screen division icon 450.

Furthermore, in an embodiment, sizes or rates of the first layer 410 and the second layer 420 may be freely changed according to a request of the therapist. In this case, the first image data or the second image data provided to each layer may be processed in response to each layer to be provided to the screen of the therapist terminal.

For example, the first image data 810 of FIG. 8 may include the entire appearance where the user 100 performs rehabilitation training using a rehabilitation training device 700 and a rehabilitation training display device 600 depending on a size and rate of the wide first layer 410.

On the other hand, a horizontal rate of the first layer 410 of FIG. 9 may become narrow due to a screen split into the first layer 410 and a second layer 420. Thus, the first image data 810 provided to the first layer 410 may be processed and provided with respect to an appearance where the user 100 which is a key element performs rehabilitation training using the rehabilitation training device 700.

Furthermore, in another embodiment, it is possible for the first layer and the second layer to be partially overlapped and provided.

Figure 10:
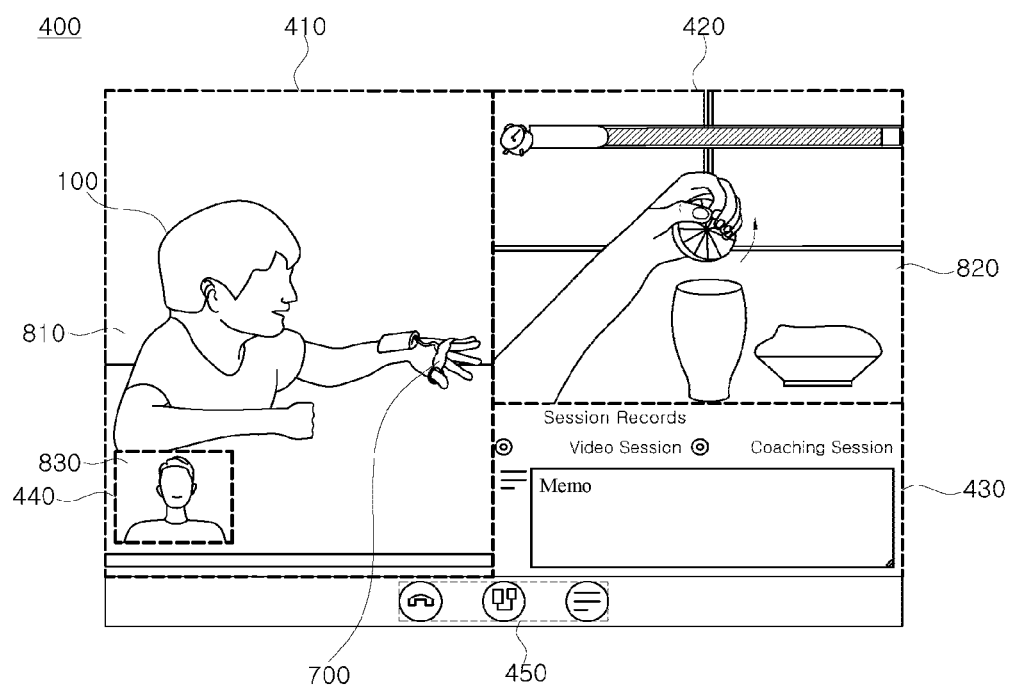
FIG. 10 is a drawing illustrating a therapist terminal screen further including a third layer according to an embodiment of the inventive concept.

FIG. 10 is a drawing illustrating a therapist terminal screen further including a third layer according to an embodiment of the inventive concept. Referring to FIG. 10, in an embodiment, the therapist terminal screen may further include a third layer 430 depending on a request of a therapist 150.

In an embodiment, the third layer 430 may provide text data or image data received from the therapist 150 and may provide text data or image data transmitted and received between the therapist 150 and a user 100.

In an embodiment, as shown in FIG. 10, the third layer 430 may be a region where the therapist 150 records and stores a memo including text and an image while viewing first image data and second image data about rehabilitation training of the user 100.

As a detailed example, the third layer 430 may be configured as a form of a document generally written for performing rehabilitation training of a patient by the therapist 150 (e.g., a report submitted to a hospital or an insurance). For example, the therapist 150 may identify first image data and second image data about rehabilitation training of the user 150 in real time, may write and store a report for a state of the user 100, and may efficiently write or submit a rehabilitation training document as a request for submitting a writing report and a report for an insurance is transmitted to a server.

In another embodiment, the third layer 430 may be a chat room capable of transmitting and receiving text or an image between the therapist 150 and the user 100.

Furthermore, in an embodiment, as shown in FIG. 10, the therapist terminal screen may further include a fourth layer 440 which provides third image data 830 about an appearance of the therapist 150. In other words, like a general video call, a screen of a therapist captured by a therapist terminal may be further displayed as well as a screen of a counterpart (user).

As described above, the first to fourth layers of the therapist terminal screen are not limited to whether each of the first to fourth layers is provided, size, or rate, and may be displayed on the therapist terminal screen to selectively include one or more of the first to fourth layers depending on a request of the therapist.

Figure 11:
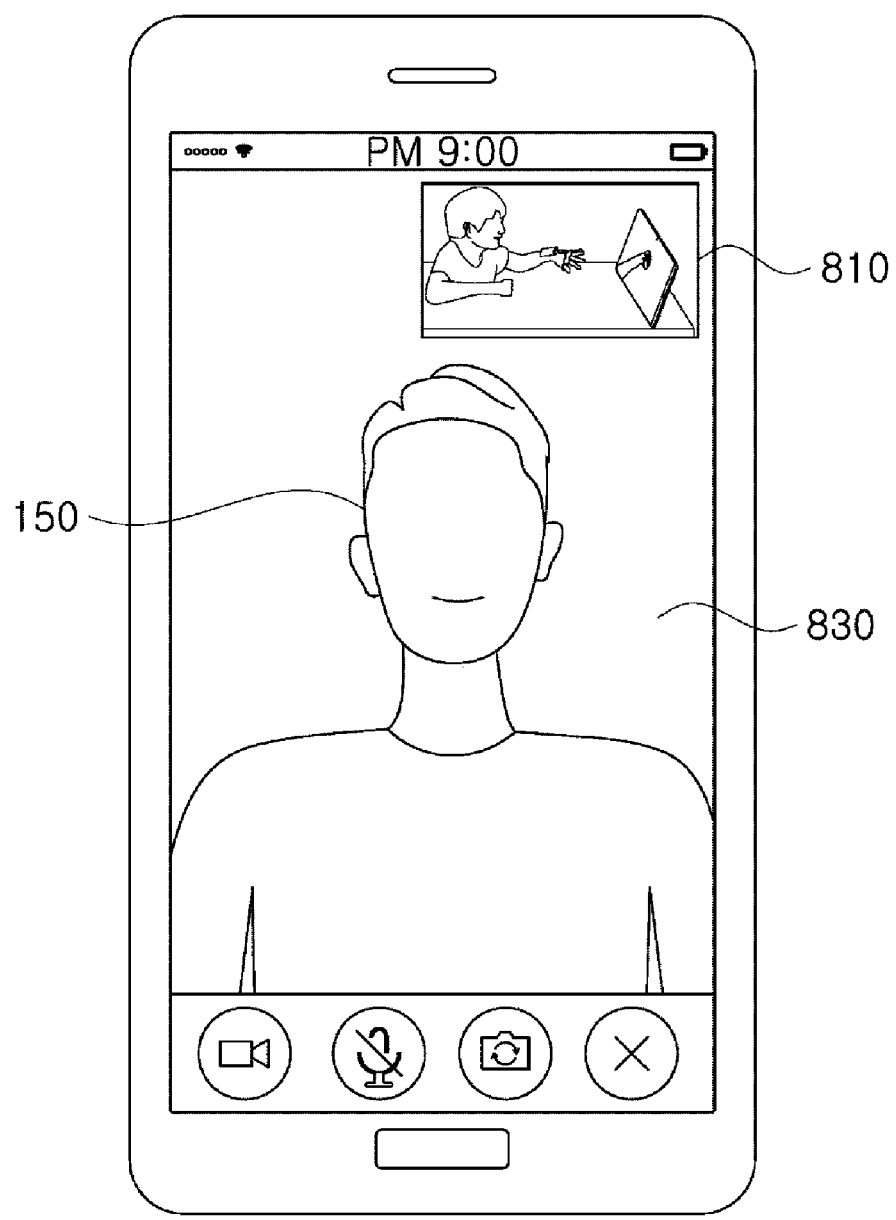
FIG. 11 is a drawing illustrating a user terminal screen which provides first image data and third image data according to an embodiment of the inventive concept.

FIG. 11 is a drawing illustrating a user terminal screen which provides first image data and third image data according to an embodiment of the inventive concept. For example, a user smartphone 500 may provide third image data 830 about a therapist 150, received from a therapist PC 400, or first image data 810, which is being captured using the user smartphone 500.

Figure 12:
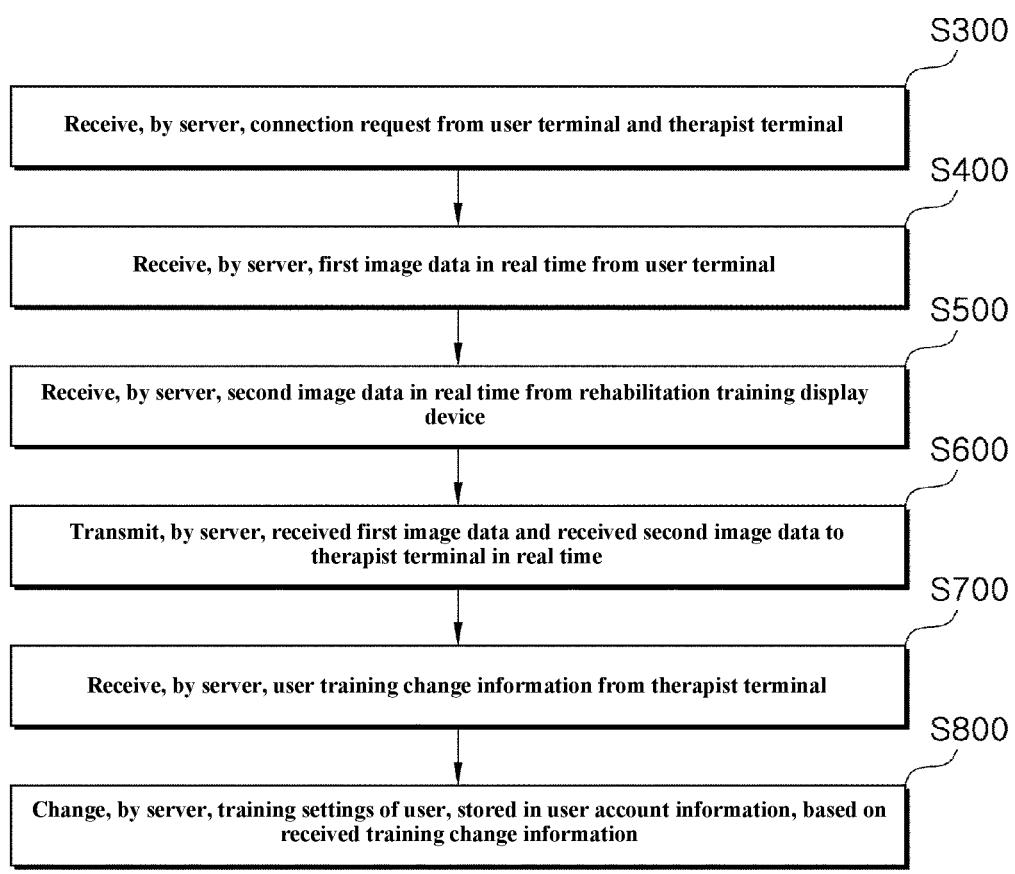
FIG. 12 is a flowchart illustrating a method for providing remote rehabilitation training, which further includes allowing a therapist to change user training settings, according to an embodiment of the inventive concept.

Referring to FIG. 12, in an embodiment, the method for providing the remote rehabilitation training may further include receiving (S700) user training change information from a therapist terminal.

In an embodiment, the user training change information may refer to information about training settings including a training type, training strength, a training rate, or a training period for rehabilitation training performed by a user. Furthermore, the training may include the above-mentioned daily life mission and information reading mission as well as rehabilitation training (e.g., an interworking training game mission) using a rehabilitation training device 700 of FIG. 1.

For example, a therapist may analyze a rehabilitation training result and a current state of the user (patient) based on the above-mentioned first image data and second image data and may transmit information about settings or changes of a rehabilitation training curriculum, such as a future rehabilitation training type, strength, and period of the user, or information about settings or changes of various missions in everyday life.

Furthermore, in an embodiment, the method for providing the remote rehabilitation training may further include changing (S800) training settings of the user, stored in the user account information, based on the training change information received from the therapist terminal.

In other words, the server may receive training change information from the therapist terminal and may change and apply settings of a training curriculum of the user or a daily life mission, stored in corresponding user account information, based on the training change information.

For example, when 'a first-stage task' is designated as the daily life mission of the user, but, when changing the 'first-stage task' to a 'second-stage task' when the therapist determines that a state of the user (patient) is improved as a result of viewing and analyzing first image data and second image data for the user (patient), the server may receive the change information and may change and apply the training settings, stored in the account information of the user, to the 'second-stage task'.

Furthermore, in an embodiment, the user may receive a notification of the change in training settings. The changed 'second-stage task' may be displayed as the daily life mission on the application installed in a user terminal.

Figure 13:
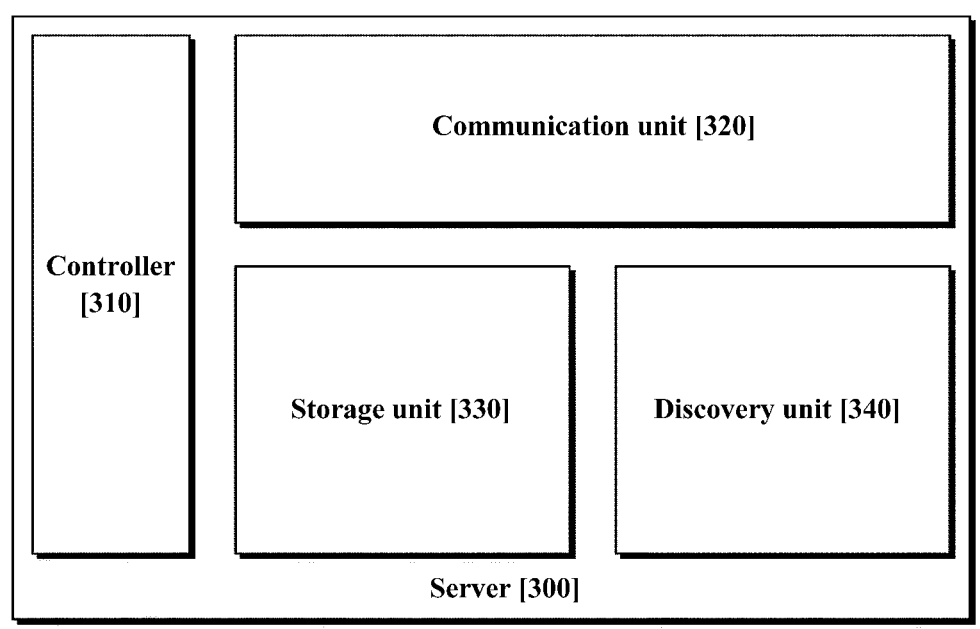
FIG. 13 is a block diagram illustrating a configuration of a server device for providing remote rehabilitation training according to an embodiment of the inventive concept.

FIG. 13 is a block diagram illustrating a configuration of a server device for providing remote rehabilitation training according to an embodiment of the inventive concept.

Referring to FIG. 13, the server device for providing the remote rehabilitation training may include a communication unit 320 for receiving a connection request from a user terminal and a therapist terminal, receiving first image data about an appearance where a user performs rehabilitation training using a rehabilitation training device in real time from the user terminal, receiving second image data, provided to the user who is performing the rehabilitation training, in real time from a rehabilitation training display device, and transmitting the received first image and the received second image data to the therapist terminal in real time and a controller 310 for controlling the communication unit 320.

In an embodiment, the rehabilitation training display device may be connected with the rehabilitation training device in a wireless or wired manner and may provide the second image data which is a screen about rehabilitation training using the rehabilitation training device to the user. The first image data may be provided to a first layer in a therapist terminal screen and the second image data may be provided to a second layer in the therapist terminal screen, depending on a request of a therapist for the provision of the first image data and the second image data a therapist for the provision of the first image data and the second image data transmitted to the therapist terminal by the communication unit 320.

Furthermore, the server device for providing the remote rehabilitation training according to another embodiment of the inventive concept may further include a storage unit 330 which stores a variety of information about remote rehabilitation training, such as identification value information of a rehabilitation training display device matched to account information or training setting information of a specific user, as a result of checking a state of a user according to user account information.

Furthermore, the server device for providing the remote rehabilitation training according to another embodiment of the inventive concept may further include a discovery unit 340 which discovers a rehabilitation training display device corresponding to user account information based on the user account information input to the user terminal. The detailed discovery method is described above.

Furthermore, the above-mentioned method for providing the remote rehabilitation training according to an embodiment of the inventive concept may be implemented as a program (or application) which is combined with a computer which is hardware to be executed and may be stored in a medium.

Operations of the method or algorithm described in connection with an embodiment of the inventive concept may be directly implemented in hardware, may be implemented with a software module executed by hardware, or may be implemented by a combination of the hardware and the software module. The software module may reside on a random access memory (RAM), a read only memory (ROM), an erasable programmable ROM (EPROM), an electrically erasable programmable ROM (EEPROM), a flash memory, a hard disc, a removable disc, a CD-ROM, or any type of computer-readable storage medium which is well known in the technical field to which the inventive concept pertains.

Embodiments of the inventive concept may have the following various effects.

First, in remote rehabilitation training, as the therapist receives a rehabilitation training screen a patient views in performing rehabilitation training, as well as an appearance of the patient who is performing the rehabilitation training, it is possible to perform more accurately remote rehabilitation training.

Secondly, the server may simply discover a rehabilitation training display device which provides a rehabilitation training screen to the patient based on account information of a patient who logs in to a program or application for providing remote rehabilitation training and may provide a rehabilitation training screen to a therapist terminal.

Thirdly, the therapist may monitor rehabilitation training of a patient and may record a memo or the like in real time or may write or submit a related document.

Finally, the therapist may set or change rehabilitation training information such as a rehabilitation training curriculum and a daily life mission, which are stored in account information of a patient to be easily coached and managed for rehabilitation training of the patient.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for providing remote rehabilitation training, the method comprising:
   receiving, by a server, a connection request from a user terminal and a therapist terminal;
   receiving, by the server, first image data including a user image of a user who is performing the rehabilitation training using a rehabilitation training device, in real time from the user terminal;
   receiving, by the server, second image data including a rehabilitation training image of the rehabilitation training using the rehabilitation training device, provided to the user who is performing the rehabilitation training, in real time from a rehabilitation training display device that is connected with the rehabilitation training device in a wireless or wired manner and provides the second image data to the rehabilitation training device;
   transmitting, by the server, the received first image data and the received second image data to the therapist terminal in real time;
   generating third image data including a document form, which has a text input field for receiving a message related to the rehabilitation training of a patient and is configured to be transmitted to at least one of a hospital server and an insurance company server as a rehabilitation training report submission, from the therapist terminal; and
   simultaneously displaying, by the therapist terminal, on a therapist terminal screen, a first layer displaying the first image data, a second layer displaying the second image data, and a third layer displaying the third image data.

2. The method of claim 1, wherein the receiving of the connection request includes:

receiving, by the server, user account information input to the user terminal and therapist account information input to the therapist terminal; and receiving, by the server, a remote rehabilitation training connection request from the user terminal and the therapist terminal, and wherein the receiving of the second image data includes:

discovering, by the server, the rehabilitation training display device corresponding to the user account information based on the user account information input to the user terminal; and receiving, by the server, the second image data in real time from the discovered rehabilitation training display device.

3. The method of claim 2, wherein the discovering of the rehabilitation training display device includes:

discovering the rehabilitation training display device to which the same account information as the user account information input to the user terminal is input.

4. The method of claim 2, further comprising:

matching, by the server, identification values of one or more rehabilitation training display devices to specific user account information, wherein the identification value is differently assigned for each specific rehabilitation training display device, and wherein the discovering of the rehabilitation training display device includes:

discovering the rehabilitation training display device of an identification value matched to the user account information input to the user terminal.

5. The method of claim 1, further comprising:

receiving, by the server, user training change information from the therapist terminal, wherein the user training change information is information about training settings including a training type, training strength, a training rate, or a training period for the rehabilitation training performed by the user.

6. The method of claim 5, further comprising:

changing, by the server, training settings of the user, stored in user account information, based on the training change information received from the therapist terminal.

7. A non-transitory computer-readable recording medium storing a program for providing remote rehabilitation training, and configured to be coupled to a hardware computer, the program includes instructions to execute the method of claim 1.

8. The method of claim 1, wherein the rehabilitation training is a daily life mission to perform actions the patient does routinely in everyday life.

9. The method of claim 1, further comprising:

transmitting the document form to at least one of the hospital server and the insurance company server as the rehabilitation training report submission.

10. An apparatus for providing remote rehabilitation training, the apparatus comprising:

a communication unit configured to receive a connection request from a user terminal and a therapist terminal, receive first image data including a user image of a user who is performing the rehabilitation training using a rehabilitation training device, in real time from the user terminal, receive second image data including a rehabilitation training image of the rehabilitation training using the rehabilitation training device, provided to the user who is performing the rehabilitation training, in real time from a rehabilitation training display device that is connected with the rehabilitation training device in a wireless or wired manner and provides the second image data to the rehabilitation training device, and transmit the received first image data and the received second image data to the therapist terminal in real time; and a controller configured to control the communication unit, generate third image data including a document form, which has a text input field for receiving a message related to the rehabilitation training of a patient and is configured to be transmitted to at least one of a hospital server and an insurance company server as a rehabilitation training report submission, from the therapist terminal, and control the therapist terminal to simultaneously display, on a therapist terminal screen, a first layer displaying the first image data, a second layer displaying the second image data, and a third layer displaying the third image data.

11. The apparatus of claim 10, wherein the rehabilitation training is a daily life mission to perform actions the patient does routinely in everyday life.

12. The apparatus of claim 10, wherein the controller is further configured to control the communication unit to transmit the document form to at least one of the hospital server and the insurance company server as the rehabilitation training report submission.

* * * * *